US008470551B2

(12) United States Patent
Sung et al.

(10) Patent No.: US 8,470,551 B2
(45) Date of Patent: Jun. 25, 2013

(54) SURFACE EXPRESSION VECTOR FOR FUSION PROTEIN OF MYO-2 PEPTIDE MULTIMER AND MYOSTATIN, AND MICROORGANISM TRANSFORMED BY THEREOF

(75) Inventors: Moon-Hee Sung, Daejeon (KR); Chul Joong Kim, Daejeon (KR); Haryoung Poo, Daejeon (KR); Ji Yeon Kim, Seoul (KR); Young Suk Kim, Jeollabuk-do (KR); Long Chun Xu, Daejeon (KR)

(73) Assignees: Bioleaders Corporation, Daejeon (KR); Korea Research Institute of Science and Technology, Daejeon (KR); The Industry and Academic Cooperation in Chungnam National University, Daejeon (KR)

( * ) Notice: Subject to any disclaimer, the term of this patent is extended or adjusted under 35 U.S.C. 154(b) by 254 days.

(21) Appl. No.: 12/682,453

(22) PCT Filed: Nov. 30, 2007

(86) PCT No.: PCT/KR2007/006147

§ 371 (c)(1),
(2), (4) Date: May 18, 2010

(87) PCT Pub. No.: WO2009/051290

PCT Pub. Date: Apr. 23, 2009

(65) Prior Publication Data

US 2010/0226891 A1 Sep. 9, 2010

(30) Foreign Application Priority Data

Oct. 15, 2007 (KR) ........................ 10-2007-0103512

(51) Int. Cl.
*C12N 15/09* (2006.01)
*C12N 1/21* (2006.01)
*C12N 15/63* (2006.01)
*C07K 1/00* (2006.01)

(52) U.S. Cl.
USPC ... 435/69.1; 435/69.7; 435/320.1; 435/252.3; 530/350

(58) Field of Classification Search
USPC ........... 435/69.1, 69.7, 320.1, 252.3; 530/350
See application file for complete search history.

(56) References Cited

U.S. PATENT DOCUMENTS 6,369,201 B1 * 4/2002 Barker et al. .............. 530/387.1
2003/0129171 A1 * 7/2003 Grobet et al. .............. 424/93.21
2004/0253704 A1 12/2004 Sung et al.
2005/0191720 A1 * 9/2005 Sung et al. ................... 435/69.1

FOREIGN PATENT DOCUMENTS

KR 10-2004-0032824 4/2004
WO 03014360 A1 2/2003

OTHER PUBLICATIONS

NCBI Locus NP_001103291.*
NCBI GenBank: EU016507.1.*
Kim et al., Poult. Sci. Jun. 2006 vol. 85 No. 6 1062-1071 Production of a monoclonal anti-myostatin antibody and the effects of in ovo administration of the antibody on posthatch broiler growth and muscle mass.*
Francisco, J.A., et al., Transport and anchoring of β-lactamase to the external surface of *Escherichia coli*, Proc. Natl. Acad. Sci. USA, Apr. 1992, pp. 2713-2717, vol. 89.
Fuchs, P., et al., Targeting Recombinant Antibodies to the Surface of *Escherichia coli*: Fusion to a Peptidoglycan Associated Lipoprotein, Bio/Technology, 1991, pp. 1369-1372, vol. 9.
Jung, H. C., et al., Expression of carboxymethylcellulase on the surface of *Escherichia coli* using Pseudomonas syringae ice nucleation protein, Enzyme and Microbial Technology, 1998, pp. 348-354, vol. 22.
Jung, H. C., et al., Surface display of *Zymomonas mobilis* levansucrase by using the ice-nucleation protein of Pseudonomas syringae, Nature Biotechnology, Jun. 1998, pp. 576-580, vol. 16.
Klauser, T., et al., Extracellular transport of cholera toxin B subunit using Neisseria IgA protease β-domain: conformation-dependent outer membrane translocation, The EMBO Journal, 1990, pp. 1991-1999, vol. 9, No. 6.
Lee, J.S., et al., Surface-displayed viral antigens on Salmonella carrier vaccine, Nature Biotechnology, Jun. 2000, pp. 645-648, vol. 18.
McPherron, A.C., et al., Regulation of skeletal muscle mass in mice by a new TGF-β superfamily member, Nature, May 1, 1997, pp. 83-90, vol. 387.
McPherron, A.C., et al., Double muscling in cattle due to mutations in the myostatin gene, Proc. Natl. Acad. Sci. USA, Nov. 1997, pp. 12457-12461, vol. 94.
Medaglini, D., et al., Mucosal and systemic immune responses to a recombinant protein expressed on the surface of the oral commensal bacterium *Streptococcus gordonii* after oral colonization, Proc. Natl. Acad. Sci. USA, Jul. 1995, pp. 6868-6872, vol. 92.
Charbit et al., Presentation of Two Epitopes of the pres2 Region of Hepatitis B Virus on Live Recombinant Bacteria, J. Immunology, pp. 1658-1664, vol. 139, No. 5, 1997.
Agterberg et al., Outer membrane PhoE protein of *Escherichia coli* as a carrier for foreign antigenic determinants: immunogenicity of epitopes of foot-and-mouth disease virus, Vaccine, 1990, pp. 85-91, vol. 8.

(Continued)

*Primary Examiner* — Maria Leavitt
(74) *Attorney, Agent, or Firm* — Tristan A. Fuierer; Andrew D. Gerschutz; Moore & Van Allen, PLLC

(57) ABSTRACT

The present invention relates to a fusion protein in which a myostatin mature protein is fused to a multimer of myostatin-derived antigenic peptide Myo-2, a surface expression vector containing a polynucleotide encoding the fusion protein, a recombinant microorganism transformed with the vector, and a feedstuff additive or a pharmaceutical composition containing the microorganism as an effective ingredient. The feedstuff additive or pharmaceutical composition according to the present invention can be used for muscle development and regulation of muscle growth in livestock and poultry, as well as for preventing and treating muscle-wasting diseases and degenerative diseases such as muscular dystrophy, muscular atrophy and the like. In addition, the transformed strain shows the same effect even if the strain itself after culture thereof is directly used, and thus it is very economical.

10 Claims, 5 Drawing Sheets

OTHER PUBLICATIONS

Felici et al., Selection of Antibody Ligands from a Large Library of Oligopeptides Expressed on a Multivalent Exposition Vector, J. Mol. Biol., 1991, pp. 301-310, vol. 222.

Hedegaard et al., Type 1 fimbriae of EscherMia cofi as carriers of heterologous antigenic sequences, Gene, 1989, pp. 115-124, vol. 85.

Kornacker et al., The normally periplasmic enzyme p-lactamase is specifically and efficiently translocated through the *Escherichia coli* outer membrane when it is fused to the cell-surface enzyme pullulanase, Mol. Microbiol., 1990, pp. 1101-1109, vol. 4, No. 7.

* cited by examiner

| | mAV72 | Myo-1 | Myo-2 | Control |
|---|---|---|---|---|
| Average | 1659.71 | 1486.44 | 1695.46 | 1502.51 |

SURFACE EXPRESSION VECTOR FOR FUSION PROTEIN OF MYO-2 PEPTIDE MULTIMER AND MYOSTATIN, AND MICROORGANISM TRANSFORMED BY THEREOF

CROSS-REFERENCE TO RELATED APPLICATIONS

This application is filed under the provisions of 35 U.S.C. §371 and claims the priority of International Patent Application No. PCT/KR2007/006147 filed on 30 Nov. 2007 entitled "Surface Expression Vector for Fusion Protein of Myo-2 Peptide Multimer and Myostatin, and Microorganism Transformed by Thereof" in the name of Moon-Hee SUNG, et al., which claims priority to Korean Patent Application 10-2007-0103512 filed on 15 Oct. 2007, both of which are hereby incorporated by reference herein in their entirety.

TECHNICAL FIELD

The present invention relates to a fusion protein in which a myostatin mature protein is fused to a multimer of myostatin-derived antigenic peptide Myo-2, a surface expression vector containing a polynucleotide encoding the fusion protein, a recombinant microorganism transformed with the vector, and a feedstuff additive or a pharmaceutical composition containing the microorganism as an effective ingredient.

BACKGROUND ART

GDF-8 (Growth Differentiation Factor-8), also called myostatin as a growth controlling factor, which selectively negative regulates skeletal muscle growth, is discovered in 1997 (McPherron et al., *Nature,* 387:83, 1997). A research team, which discovered myostatin, has announced that two high quality cow breeds due to their high muscular mass and tender meat, i.e., Belgian blue and Piedmontese, have mutation in gene encoding myostatin, which results in muscle development (McPherron and Lee, *Proc. Natl. Acad. Sci. USA.,* 94:12457, 1997), and reported that double-muscle animals of these breeds have average muscle mass increased by 20~25% based on that of ordinary animals.

Experimentally, myostatin-knockout mice also showed significant increases in skeletal muscle mass, and muscles isolated from myostatin-negative mice were about 2- to 3-fold heavier than muscles isolated from wild mice. It has been reported that knockout mice have about 35% higher total body weight than that of wild mice and myostatin-deficient mice have 80% more muscle fibers than that of normal mice, and the increment of skeletal muscle observed in the knockout mice is caused by abnormal growth of muscle fibers as well as an increase in the number of muscle fibers.

Myostatin as a growth controlling factor, which selectively negative regulates skeletal muscle growth, belongs to TGF-$\alpha$ (transforming growth factor-$\alpha$) super family, is composed of 375 amino acid precursors, and has the same C-terminal fragments of about 109 amino acid residues in mice, rats, human, swine, fowl and turkey and only 3 amino acid residues in the C-terminal region thereof are not the same in monkeys, cows, and sheep. The C-terminal regions are expected to include physiologically active portion of myostatin. Myostatin has shown a high degree of conservation along evolution among various species, which implies that myostatin is an essential factor in biological muscle control (McPherron and Lee, *Proc. Natl. Acad. Sci. USA.,* 94:12457, 1997).

Myostatin expression is limited to skeletal muscle and it is expressed at low levels in adipose tissue. It seems that myostatin functions as a negative regulator of skeletal muscle growth, but the physiological role of myostatin in an adult individual is not known. Although studies on the physiological role of myostatin have been focused on abnormal growth or its regeneration ability after muscle damage, it is also known that myostatin inhibits adipose tissue growth. However, it has not been known yet whether myostatin acts locally or systemically to regulate animal growth.

Recently, various studies are being conducted on inactivating or inhibiting myostatin exerting the role for negative regulation of skeletal muscle growth. Representative studies thereof include the development of therapeutic agents for treatment of human diseases including muscle-wasting diseases such as muscular dystrophy or muscular atrophy, or muscle loss caused by AIDS, cancer and the like, and an attempt to develop feedstuff additives for growing livestock with high quality meat. Moreover, since, when myostatin was developed as supplement additives for muscle enhancement, it inhibited body fat accumulation due to an increase in the amount of muscle, it is expected to be effective for obesity treatment, and thus, studies thereon are also being conducted.

Two representative studies on a method for inducing muscle growth by inhibiting the function of myostatin protein, are being conducted. One is to discover and use various proteins (follastatin, mutant activin type II receptor, myostatin propeptide, etc.) which inhibit myostatin activity to suppress its function, and the other is to produce antibodies against myostatin polypeptide by animal immunization using myostatin polypeptide, a subsequence thereof, and mutant subsequences.

It was reported that the production of antibodies against myostatin immunogens in vertebrate animals results in a reduction in endogenous myostatin activity, thus showing biological effects such as body weight gain, increased muscle mass, an increase in the number of muscle cells, an increase in muscle cell size, a decrease in the amount of body fat, an increase in muscular strength and the like. However, because the number and type of muscle fibers are genetically programmed during embryogenesis, a decrease in myostatin activity does not lead an increase in the number of muscle fibers in fully grown breeding animals, which may negatively affect meat quality, breed characteristics and fat ratio, but an increase in body weight and growth rate caused by abnormal muscle growth in animals showing a decrease in myostatin activity provides effective methods in the production of beef, pork and poultry meat.

However, most of the studies are conducted by artificially synthesizing myostatin polypeptide or the subsequence thereof, or preparing by isolation and purification after expressing them in *Escherichia coli*, which results in economic inefficiency and thus it is difficult to apply them to industrial applications.

In livestock industry, various breeding programs to enhance the growth rate of animals by increasing feedstuff efficiency are being developed and improved. Among them, medical approaches include methods of administering antibiotics or antibiotic-like compounds to breeding animals, or administering hormones such as growth hormones to them. However, administration of antibiotics or antibiotic-like compounds to breeding animals is banned, since it can cause a problem of inducing antibiotic cross-resistance. Additionally, in the case of administration of growth hormone to breeding animals, it is disadvantageous in that it costs a lot, short period of treatment should be repeated because of a short half-time of growth hormone, and growth hormone remaining in meat obtained from animals treated therewith may cause health problems in humans. Because of the difficulties in the medical approaches, various breeding programs to enhance the growth rate of animals by increasing feedstuff efficiency, are being continuously developed.

Technology of expressing by attaching a desired protein to the cellular surface of microorganisms is referred to as a cell surface display technology. The cell surface display technology is to express a foreign protein on the cellular surface using the surface protein of microorganisms, such as bacteria or yeasts, as a surface anchoring motif, and is used in a wide range of applications, including the production of recombinant live vaccines, the construction and screening of peptide/antibody libraries, whole cell absorbents and bioconversion catalysts. The application range of this technology is determined depending on what kind of protein is expressed on the cell surface, thus the industrial application potentiality of the cell surface display technology can be said to be significant.

For successful cell surface display, a surface anchoring motif is most important. Selection and development of a motif capable of effectively expressing a foreign protein on the cell surface is the core of this technology. Accordingly, a surface anchoring motif with the following properties should be selected. First, it should have a secretory signal helping the foreign protein to pass through an intracellular membrane, and to reach to the cell surface. Second, it should have a target signal helping the foreign protein to be stably attached to the outer surface of the cell membrane. Third, it should be expressed on the cell surface at large amounts but has little or no effect on the growth of cells. Fourth, it should be stably expressed regardless of the protein size, without causing a change in the three-dimensional structure of the foreign protein. However, a surface anchoring motif satisfying all the above requirements have not yet been developed.

Cell surface anchoring motifs, which have been known and used till now, are broadly classified into four kinds, i.e., outer membrane proteins, lipoproteins, secretory proteins, and surface proteins such as flagella proteins. In the case of gram-negative bacteria, proteins present in the outer cell membrane, such as LamB, PhoE (Charbit et al., *J. Immunol.,* 139:1658, 1987; Agterberg et al., *Vaccine,* 8:85, 1990) and OmpA, were mainly used. Moreover, lipoproteins, such as TraT (Felici et al., *J. Mol. Biol.,* 222:301, 1991), PAL (peptidoglycan associated lipoprotein) (Fuchs et al., *Bio/Technology,* 9:1369, 1991) and Lpp (Francisco et al., *Proc. Natl. Acad. Sci. USA.,* 489:2713, 1992), were also used. Furthermore, the expression of foreign proteins was also attempted using FimA, a fimbriae protein such as the FimH adhesin of type 1 fimbriae (Hedegaard et al., *Gene,* 85:115, 1989), or a pili protein such as a PapA pilus subunit as surface anchoring motifs. In addition, it was reported that an ice nucleation protein (Jung et al., *Nat. Biotechnol.,* 16:576, 1998; Jung et al., *Enzyme Microb. Technol.,* 22:348, 1998; Lee et al., *Nat. Biotechnol.,* 18:645, 2000), pullulanase of *Klebsiella oxytoca* (Kornacker et al., *Mol. Microbiol.,* 4:1101, 1990), IgA protease of *Neisseria* (Klauser et al., *EMBO J.,* 9:1991, 1990), *E. coli* adhesin AIDA-1, VirG protein of *Shigella*, a fusion protein of Lpp and OmpA, can be used as surface anchoring motifs.

In the case of using Gram-positive bacteria, there is a report that a malaria antigen was effectively expressed using *Staphylococcus aureus*-derived protein A and FnBPB protein, as surface anchoring motifs. In addition, it was reported that surface coat protein of lactic acid bacteria was used in surface expression and surface protein of Gram-positive bacteria such as a *Streptococcus pyogenes*-derived M6 protein (Medaglini, D et al., *Proc. Natl. Acad. Sci. USA.,* 92:6868, 1995), S-layer protein EA1 of *Bacillus anthracis, Bacillus subtilis* CotB, etc., were also used as surface anchoring motifs.

Meanwhile, the present inventors already developed a novel vector effectively expressing a foreign protein on the surface of microorganisms using a pgsBCA gene encoding a *Bacillus* sp. strain-derived poly-gamma-glutamate synthetase complex as a new surface anchoring motif, as well as a method for expressing a large amount of foreign protein on the surface of microorganisms transformed with the vector (Korea Patent Registration No. 10-0469800).

Many studies were performed in an attempt to stably express the antigen or epitope of pathogenic organisms in bacteria where mass production is possible by genetic engineering techniques using the above-described surface anchoring motifs. It was reported that, particularly when a foreign immunogen expressed on the surface of non-pathogenic bacteria is orally administered alive, a more lasting and strong immune response than that of the prior vaccine using attenuated pathogenic bacteria or viruses, can be induced. This induction of the immune reaction is induced by an in vivo immune response to the live bacteria, which is known to be because the surface structures of the bacteria act as adjuvants increasing the antigenicity of the surface-expressed foreign protein. The development of a recombinant live vaccine of non-pathogenic bacteria using this surface expression system is noticeable.

Accordingly, the present inventors have made extensive efforts to develop a method for effectively expressing a myostatin fusion protein, capable of inducing a strong immunogenicity against myostatin, on the surface of a microorganism, and as a result, they found that, when a fusion protein, in which a multimer of Myo-2 peptide is fused to myostatin, was expressed on the surface of lactic acid bacteria using a pgsBCA gene encoding *Bacillus* sp. strain-derived poly-gamma-glutamate synthetase complex as a surface anchoring motif, said fusion protein was effectively expressed on the surface thereof, and confirmed that oral administration of lactic acid bacteria expressing said fusion protein on the cell surface increased antibody production in blood, as well as, body weight and muscle mass, thereby completing the present invention.

SUMMARY OF THE INVENTION

The object of the present invention is to provide Myo-2 peptide derived from myostatin and a multimer of said Myo-2 peptide.

Another object of the present invention is to provide a fusion protein in which a myostatin mature protein is fused to said Myo-2 peptide multimer.

Still another object of the present invention is to provide a cell surface expression vector comprising a gene encoding said fusion protein and a recombinant microorganism transformed with said surface expression vector.

Yet another object of the present invention is to provide a method for preparing a microorganism expressing said fusion protein on the cell surface.

Further, another object of the present invention is to provide a feedstuff additive comprising said fusion protein or a microorganism expressing said fusion protein on the cell surface.

Still further another object of the present invention is to provide a pharmaceutical composition comprising said fusion protein or a microorganism expressing said fusion protein on the cell surface.

To achieve the above object, the present invention provides a myostatin-derived Myo-2 peptide having an amino acid sequence of SEQ ID NO: 1, and a Myo-2 peptide multimer consisting of 2~8 of the myostatin-derived Myo-2 peptide.

The present invention also provides a fusion protein in which said Myo-2 multimer is fused to a myostatin mature protein.

The present invention also provides a cell surface expression vector containing a gene encoding a myostatin mature protein and a nucleotide sequence encoding the Myo-2 peptide multimer operatively linked to one or more genes selected from the group consisting of pgsB, pgsC and pgsA genes encoding poly-gamma-glutamate synthetase complex, and a recombinant microorganism transformed with said surface expression vector.

The present invention also provides a method for preparing a microorganism, which has a fusion protein, containing a myostatin mature protein fused to a multimer of myostatin-derived peptide (Myo-2), expressed on the cell surface, which comprises the steps of: (a) expressing a fusion protein, containing a myostatin mature protein fused to a multimer of myostatin-derived peptide, on the cell surface by culturing said recombinant microorganisms; and (b) collecting the microorganisms expressing the fusion protein containing a myostatin mature protein fused to a multimer of myostatin-derived peptide on the cell surface.

In addition, the present invention provides a feedstuff additive for promoting muscle growth or improving body weight gain in animals, which comprises a microorganism expressing said fusion protein, on the cell surface as an effective ingredient.

Moreover, the present invention provides a composition for promoting muscle growth or improving body weight gain in animals, which comprises a microorganism expressing said fusion protein, on the cell surface as an effective ingredient.

The present invention also provides a pharmaceutical composition for preventing or treating degenerative diseases or muscle-wasting diseases, which comprises a microorganism expressing said fusion protein, on the cell surface as an effective ingredient.

Moreover, the present invention provides a feedstuff additive for promoting muscle growth or improving body weight gain in animals, which comprises said fusion protein as an effective ingredient.

The present invention also provides a composition for promoting muscle growth or improving body weight gain in animals, which comprises said fusion protein as an effective ingredient.

The present invention also provides a pharmaceutical composition for preventing or treating degenerative diseases or muscle-wasting diseases, which comprises said fusion protein as an effective ingredient.

In addition, the present invention provides a method for increasing the size or number of muscle cells in animals, which comprises administrating said feedstuff additive or pharmaceutical composition to animals.

The above and other objects, features and embodiments of the present invention will be more clearly understood from the following detailed description and accompanying claims.

DETAILED DESCRIPTION OF THE INVENTION, AND PREFERRED EMBODIMENTS

Figure 1:
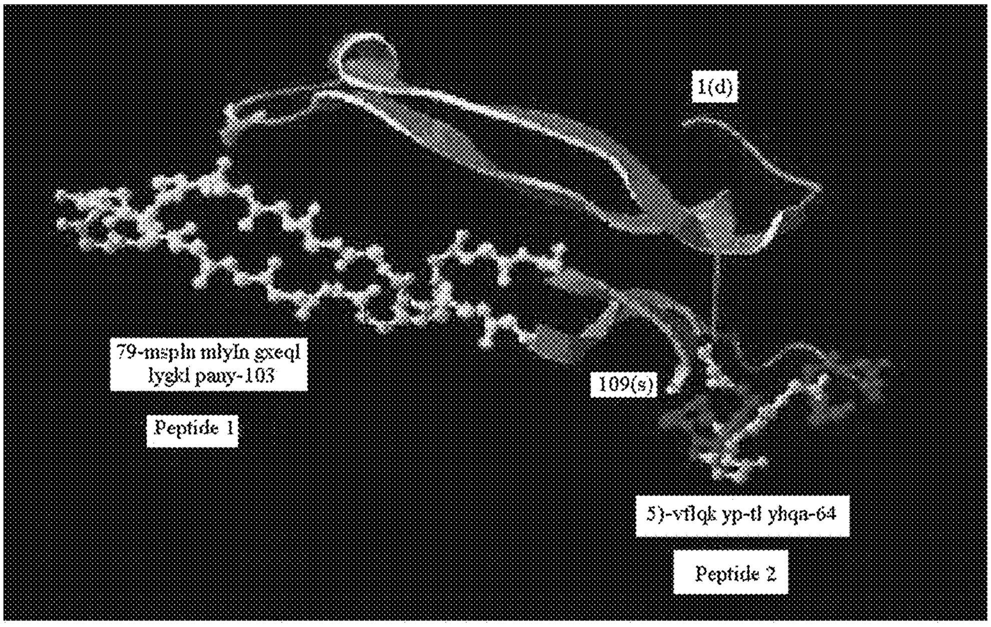
FIG. 1 is the predicted 3D structure of a chicken myostatin mature protein and antigenic regions (Myo-1, Myo-2), according to the present invention

In one aspect, the present invention relates to a myostatin-derived Myo-2 peptide having an amino acid sequence of SEQ ID NO: 1, and a Myo-2 peptide multimer consisting of 2~8 of the myostatin-derived Myo-2 peptide, and a fusion protein in which the myostatin mature protein is fused to the Myo-2 peptide multimer.

In the present invention, a Myo-2 peptide was selected based on the predicted 3D structure of a myostatin mature protein and the Myo-2 peptide was administered to broiler breeders, and as a result, it was confirmed that chicks hatched from eggs laid by the broiler breeder hens injected with the Myo-2 peptide, showed increased body weight gain.

Myostatin-derived peptide Myo-2 according to the present invention shows antigenicity against myostatin protein in the body, which enables individuals immunized with Myo-2 to gain weight, and the Myo-2 peptide multimer is obtained by multimerizing 2~8 of Myo-2 peptide in order to enhance the antigenicity of Myo-2 against myostatin. A fusion protein obtained by combining a myostatin mature protein with said Myo-2 peptide multimer shows a remarkably high antigenicity against myostatin and thus increases muscle mass.

In the present invention, in order to obtain a fusion protein, in which a myostatin mature protein is fused to a Myo-2 peptide multimer, expressed on the surface of a microorganism, a fusion protein, in which a fusion protein comprising a myostatin mature protein fused to a Myo-2 peptide multimer is fused to poly-gamma-glutamate synthetase complex, was constructed.

In the present invention, the poly-gamma-glutamate synthetase complex, which is an outer membrane protein encoded by pgsB, pgsC and pgsA genes, has a lot of advantages as a surface anchoring motif expressing foreign proteins on a cell surface due to primary structure of amino acids and properties thereof. That is, it has advantages in that: first, it can be abundantly expressed on a cell surface for the synthesis and extracellular secretion of poly-gamma-glutamate; second, the outer membrane protein involved in synthesizing the expressed poly-gamma-glutamate is also maintained stably during the resting stage of cell cycle; third, it has structures (especially, in case of pgsA) protruding from the cell surface; and fourth, since the outer membrane protein (pgsBCA) is originated from the surface of gram positive bacteria, it can be stably expressed on the surface of gram negative bacteria as well as gram positive bacteria.

In the present invention, as a cell surface expression vector containing genes (pgsB, pgsC and pgsA) encoding said poly-gamma-glutamate synthetase complex, a cell surface expression vector, which is constructed by obtaining pgsBCA from all of *Bacillus* sp. strains producing poly-gamma-glutamate, may be used, and preferably, a cell surface expression vector containing an outer membrane protein gene involved in synthesizing poly-gamma-glutamate derived from *Bacillus subtilis* var. *chungkookjang* (KCTC 0697BP), but it is not limited thereto. For example, the use of an expression vector, which is prepared by using other strain-derived pgsBCA gene having a homology of at least 80% with a base sequence of pgsBCA genes present in *Bacillus subtilis* var. *chungkookjang*, will also be within the scope of the present invention.

In another aspect, the present invention relates to a cell surface expression vector containing a gene encoding a myostatin mature protein and a nucleotide sequence encoding the Myo-2 peptide multimer operatively linked to one or more genes selected from the group consisting of pgsB, pgsC and pgsA genes encoding poly-gamma-glutamate synthetase complex, and a recombinant microorganism transformed with said surface expression vector.

In the present invention, said myostatin is preferably derived from mammals or birds (poultry). And said recombinant microorganism is preferably any one selected from the group consisting of *E. coli, Salmonella typhi, Salmonella typhimurium, Vibrio cholerae, Mycobacterium bovis, Shigella, Bacillus*, lactic acid bacteria, *Staphylococcus, Corynebacteria, Listeria monocytogenes* and *Streptococcus*, and more preferably, the recombinant microorganisms is lactic acid bacteria.

The myostatin in the present invention is a growth controlling factor which selectively negative regulates skeletal muscle growth, belongs to TGF-α (transforming growth factor-α) super family, and is composed of 375 amino acid precursors, and in the present invention, the mature domain of myostatin protein is a portion obtained by deleting secretion signal and prodomain from the amino acid precursors, which shows myostatin activity.

In the present invention, the myostatin is preferably derived from mammals, birds, or fish. The myostatin has shown a high degree of conservation along evolution among various species and has the same C-terminal fragments of about 109 amino acid residues in mice, rats, human, swine, chickens and turkeys and only 3 amino acid residues in the C-terminal region thereof are not the same in monkeys, cows, and sheep. It is expected that these C-terminal region would include biologically active portion of myostatin.

In still another aspect, the present invention relates to a method for preparing a microorganism, which has a fusion protein, containing a myostatin mature protein fused to the multimer of myostatin-derived peptide (Myo-2), expressed on the cell surface, which comprises the steps of: (a) expressing a fusion protein, containing a myostatin mature protein fused to a multimer of myostatin-derived peptide, on the cell surface by culturing said recombinant microorganisms; and (b) collecting the microorganisms expressing the fusion protein, containing a myostatin mature protein fused to a multimer of myostatin-derived peptide, on the cell surface.

The inventive fusion protein is expressed in a form fused with poly-gamma-glutamate synthetase protein encoded by pgsB, pgsC and pgsA, which is a poly-gamma-glutamate synthetase complex contained in the expression vector, and the fusion protein is transferred onto the surface of the microorganism by said poly-gamma-glutamate synthetase protein and located thereon.

Since the fusion protein is expressed on the surface of a microorganism without losing its function, they can be used with the protein being expressed on the surface of the microorganism, and thus they can be administered to animals with the protein being expressed on the surface of the microorganism to induce immune reaction against myostatin in animal body.

According to the present invention, when the microorganism expressing the fusion protein, in which a myostatin mature protein is fused to a multimer of myostatin-derived peptide, on the cell surface was orally administered to mice, antibodies against the fusion protein were effectively produced, and the mice showed weight gain compared to control mice orally administered with a microorganism expressing no fusion protein on the cell surface. Additionally, it showed high inhibition effect on myostatin signaling in muscle cells.

Moreover, antibody titer against chicken myostatin was high in broiler administered with the inventive microorganism expressing a fusion protein, in which a myostatin mature protein is fused to a multimer of myostatin-derived peptide, on the cell surface, and the broilers showed increased body weight gain compared to the control group.

In yet another aspect, the present invention relates to a feedstuff additive for promoting animal muscle growth or improving animal weight gain, which comprises the microorganism prepared by the above method and expressing a fusion protein containing a myostatin mature protein fused to the multimer of myostatin-derived peptide, on the cell surface, as an effective ingredient.

In further another aspect, the present invention relates to a composition for promoting animal muscle growth or improving animal weight gain, which comprises the microorganism prepared by the same method and expressing a fusion protein containing a myostatin mature protein fused to the multimer of myostatin-derived peptide, on the cell surface, as an effective ingredient.

In still further another aspect, the present invention relates to a pharmaceutical composition for preventing or treating degenerative diseases or muscle-wasting diseases, which comprises the microorganism prepared by the above method and expressing a fusion protein, containing a myostatin mature protein fused to the multimer of myostatin-derived peptide, on the cell surface, as an effective ingredient.

In yet further another aspect, the present invention relates to a method for increasing the size or number of muscle cells in animals by administering said feedstuff additive or composition to animals. In the present invention, said administration is preferably oral administration.

The inventive pharmaceutical composition for preventing or treating degenerative diseases or muscle-wasting diseases is an oral human vaccine, and can be used for preventing and treating degenerative diseases and muscle-wasting diseases such as muscular dystrophy and muscular atrophy.

The inventive pharmaceutical composition may be administered orally, ingested as food, injected subcutaneously or peritoneally, or administered rhinally to animals including human.

The induction of myostatin antibody using the inventive myostatin fusion protein and the method of decreasing myostatin activity by the induced antibodies do not cause problems related to cross-resistance in pathological microorganisms, and homology between other members of TGF-α family and myostatin sequences is a very low homology of 30-40% at amino acid level, and thus, it will not cause a problem with regard to cross-reactivity of the antibodies against endogenous myostatin (GDF-8) in vivo In addition, there is no possibility of externally administered growth hormones remaining in meat obtained from animals. Moreover, ethical problems (many calves are born by Caesarean section and the size of other organs are reduced) associated with the production of cow breeds such as Piemontese and Belgian Blue can be completely solved by down-regulating myostatin expression until the period of full growth after birth. In fact, double-muscle animals of these breeds do not need to deliver calves and thus these animals reared for meat production do not need anti-myostatin treatment.

The pharmaceutical composition of the present invention can be formulated as various preparations, for example, an oral preparation such as powders, granules, tablets, capsules, suspensions, emulsions, syrups and aerosols, a preparation for external use, a suppository and a sterile injectable preparation, according to conventional methods. The inventive composition may also be formulated with carriers, excipients and diluents such as lactose, dextrose, sucrose, sorbitol, mannitol, xylitol, erythritol, maltitol, starch, gum acasia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, tarc, magnesium stearate and mineral oil.

For the preparation, the pharmaceutical composition can be formulated with diluents or excipients such as fillers, extenders, binders, wetting agent, disintegrants and surfactants. Examples of solid preparation for oral administration include tablets, pills, powders, granules, capsules and so on, and the solid preparation is formulated by mixing at least one excipients, for example, starch, calcium carbonate, sucrose, lactose, gelatin, etc to the pharmaceutical composition. In addition to excipients, lubricants such as magnesium stearate, tarc, etc. may also be used in the composition of this invention. Examples of liquid preparation for oral administration include suspensions, solutions, emulsions, syrups, etc., and such liquid forms may contain diluents such as water and liquid paraffin, and excipients such as wetting agents, sweetening agents, flavoring agents, preservatives, etc. Examples of the formulation for the parenteral administration include sterile aqueous solution, non-aqueous solutions, suspensions, emulsions, lyophilized preparation and suppositories. Injectable ester such as ethyl olate and vegetable oil such as propylene glycol and olive oil may be used for non-aqueous solution and suspensions. The suppository preparation can be prepared by using a base such as witepsol, macrogol, Tween 61, cacao oil, laurin oil, glycerol-gelatin, etc.

The amount of the inventive pharmaceutical composition actually administered will be determined in the light of the relevant circumstances, including the patient's weight, the condition to be treated, the severity of the patient's symptoms, the period and selected route of administration, the type of drugs, and the like, but according to a person skilled in the art, the composition can be properly administered The inventive composition can be administered in a single daily dose or in multiple doses per day. Suitable doses of the composition are 10~500 mg/kg per day, and preferably 50~300 mg/kg per day to achieve the desired effect. However, the above dosage ranges are not intended to limit the scope of the present invention in any way.

The pharmaceutical composition of the present invention can be administrated via a variety of routes to mammals, including rats, mice, livestock, humans, etc. The route of administration includes oral, rectal or intravenous, intramuscular, subcutaneous, endometrium, intracerebroventicular routes of administration.

EXAMPLES

Hereinafter, the present invention will be described in more detail by examples. It is to be understood, however, that these examples are for illustrative purpose only and are not construed to limit the scope of the present invention.

Particularly in the following examples, although the mature form of myostatin was employed as the myostatin gene used for the fusion protein, gene encoding proteins capable of enhancing immunity against myostatin mature protein can also be used in combination therewith.

Furthermore, although pgsBCA among outer membrane protein genes involved in the synthesis of poly-gamma-glutamate was obtained from *Bacillus subtilis* var. *chungkookjang* (KCTC 0697BP) to use in the following examples, either vectors prepared with pgsBCA gene obtained from all *Bacillus* sp. producing poly-gamma-glutamate, or microorganisms transformed with these vectors, will also be within the scope of the present invention. For example, either the preparation of vaccine vectors using other strain-derived pgsBCA gene having a homology of at least 80% with the base sequence of pgsBCA gene present in *Bacillus subtilis* var. *chungkookjang*, or the use thereof, will also be within the scope of the present invention Moreover, although a surface expression vector was prepared only with a pgsA gene among pgsBCA genes in the following examples, as analogized from the indirect examples, the construction of vaccine vectors with all or parts of the pgsBCA genes will also be within the scope of the present invention.

Furthermore, in the following examples, only *Lactobacillus* was used as a host for the expression vector, but it will also be obvious to a person skilled in the art that the same results can be obtained, when gram-negative or gram-positive bacteria other than such bacteria are transformed by the inventive method.

Also in the following examples, only the case, where microorganisms themselves transformed with the vaccine vectors were applied to mice, fowl and pigs, is presented. However, in view of the knowledge in the field of animal feedstuff additives and vaccine-related technologies, it is to be understood that, even when either myostatin mature protein crudely extracted from said microorganisms or expressed proteins purified from said microorganisms are applied to animals, the same results can be obtained.

Example 1

Determination of Antigenic Sites on Myostatin Peptide

In order to enhance induction of immunity against myostatin, two antigenic sites on myostatin peptide (Myo-1 and Myo-2) determined on the basis of the predicted 3D structure of myostatin mature protein, and myostatin mature protein were purified and administrated transdermally to broiler breeder hens. Chicks were hatched from eggs of the immunized hens, and the enhanced growth rates between chicks were compared.

As shown in FIG. 1, Myo-1 (SEQ ID NO: 2) and Myo-2 (SEQ ID NO: 1) were determined as antigenic sites on the peptide, based on the predicted 3D structure of myostatin mature protein. In the experiment, three experimental groups; a purified myostatin mature protein-administered group (mAV group), a Myo-1-administered group and a Myo-2-administered group, and a control group were used, and each group consisted of 5 breeders (4 females and 1 male).

For primary transdermal administration, 1 mg of soluble, mature myostatin protein obtained by purifying chicken myostatin gene (SEQ ID NO: 4) expressed in *E. coli* and each 1 mg of synthesized peptides, Myo-1 and Myo-2 (Anygen, Korea) conjugated with KLH as a carrier protein mixed with complete Freund's adjuvant at a mixing ratio of 1:1, were administered transdermally to female breeders. After 3 weeks, each peptide mixed with incomplete Freund's adjuvant at a mixing ratio of 1:1 was administered transdermally to the female breeders for secondary transdermal administration. And after another 3 weeks, tertiary transdermal administration was performed in the same manner as the secondary transdermal administration. Chicks hatched from eggs laid by the immunized breeder hens, were reared until 28 days of age, and body weight gain was measured for chicks in each group.

Figure 2:
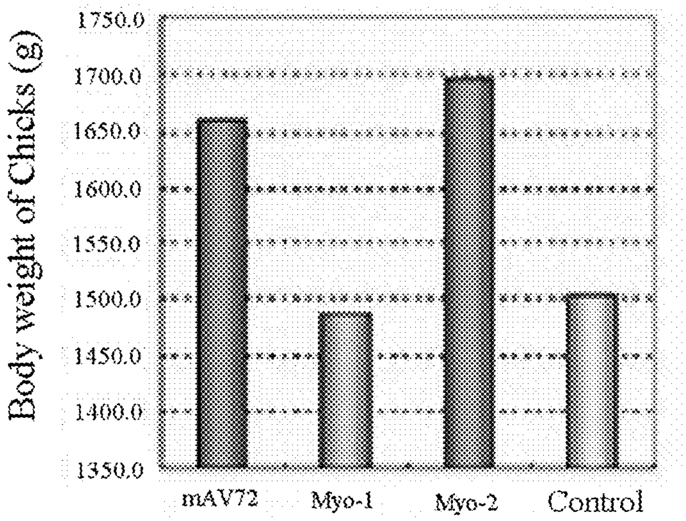
FIG. 2 shows the rate of body weight gain of chicks hatched from eggs laid by broiler breeders immunized with antigenic peptides and a chicken myostatin mature protein according to the present invention.

As described above, as a result of analyzing body weight gains of chicks reared until 28 days of age which is the time when they are ready for market, as shown in FIG. 2, in the purified myostatin mature protein-administered group (mAV group), chicks showed a 10% increase in body weight (body weight gain) compared to a control group, chicks in the group administered with Myo-2 peptide showed a 13% increase in body weight, which is the highest increase, and chicks in the group administered with Myo-1 peptide showed no increase in body weight compared with the control. Therefore, it was confirmed that administration of purified myostatin mature protein and Myo-2 peptide to broiler parent chickens induces high body weight gain in offspring chicks due to maternal antibody transmission.

Example 2

Construction of 4Myo-2 Peptide Multimer (4xMyo-2) and a Surface Expression Vector (pHCE2LB:pgsA-4-xMyo-2-CMyom)

A multimer whose repeat number is a multiple of four was constructed using a gene encoding Myo-2 peptide in chicks showed the highest body weight gain among chicks hatched from eggs laid by breeder hens administered with a myostatin-derived peptide and myostatin mature protein (4xMyo-2), and fused at its C-terminal to a gene encoding chicken myostatin mature protein (CMyom), thus constructing a surface expression vector pHCE2LB:pgsA-4-xMyo-2-CMyom.

Figure 3:
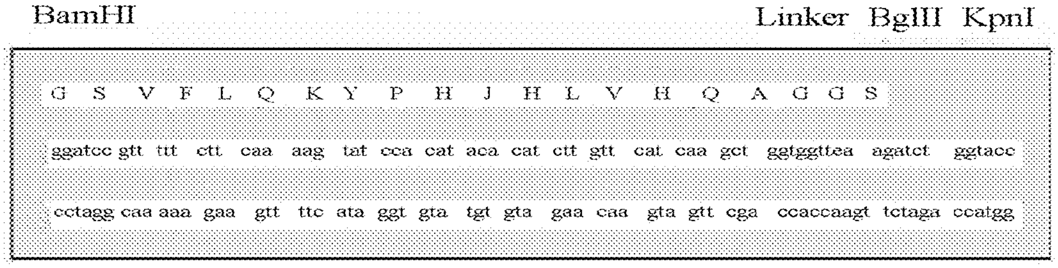
FIG. 3 shows the structure of a subunit for constructing the Myo-2 peptide multimer according to the present invention.

In order to synthesize a subunit for constructing 4Myo-2 peptide multimer, primers having the nucleotide sequences of SEQ ID NO: 5 and SEQ ID NO: 6 were diluted to a concentration of 10 pM/μl, respectively, mixed at equal volume, and allowed to react at 37° C. for 1 hour, followed by forming Myo-2 subunit digested on both sides with BamHI and KpnI as shown in FIG. 3, thus constructing pRSET(A):Myo-2 by inserting Myo-2 subunit into the sites of restriction enzymes, BamHI and KpnI of pRSET(A) vector (Invitrogen, USA).

```
SEQ ID NO: 5:
5'-gatccgtttttcttcaaaagtatccacatacacatcttgttcatcaa
gctggtggttcaagatct ggtac-3'

SEQ ID NO: 6:
5'-cagatcttgaaccaccagcttgatgaacaagatgtgtatgtggatac
ttttgaagaaaa acg-3'
```

PCR reaction was performed using a 1.3 kb of chicken myostatin gene cloned into pCRT7/NT-TOPO (Invitrogen, USA) as a template and primers having the nucleotide sequences of SEQ ID NO: 7 and SEQ ID NO: 8 to amplify a gene encoding chicken myostatin mature protein. The amplified fragments cut with restriction enzymes BglII and KpnI were inserted into BglII and KpnI restriction sites of pRSET (A):Myo-2 vector, thus constructing pRSET(A):Myo-2-CMyom vector.

```
SEQ ID NO: 7:
5'-agatctgtcgacgaggtcagagttacagac-3'

SEQ ID NO: 8:
5'-ggtacctctagattattagtcgactcatgagcacccgcaacg-3'
```

DNA fragments obtained by digesting said pRSET(A):Myo-2-CMyom vector with restriction enzymes BamHI and KpnI was ligated to a vector obtained by digesting pRSET (A):Myo-2-CMyom with restriction enzymes BglII and KpnI using T4 ligase, thus constructing a vector pRSET(A):2xMyo-2-CMyom containing repeats of a gene encoding two subunits of Myo-2 peptide.

Using the same method as the above, pRSET(A):4xMyo-2-CMyom was constructed by repeatedly inserting 2XMyo-2-CMyom into BglII and KpnI restriction sites of pRSET(A):2xMyo-2-CMyom.

Figure 4:
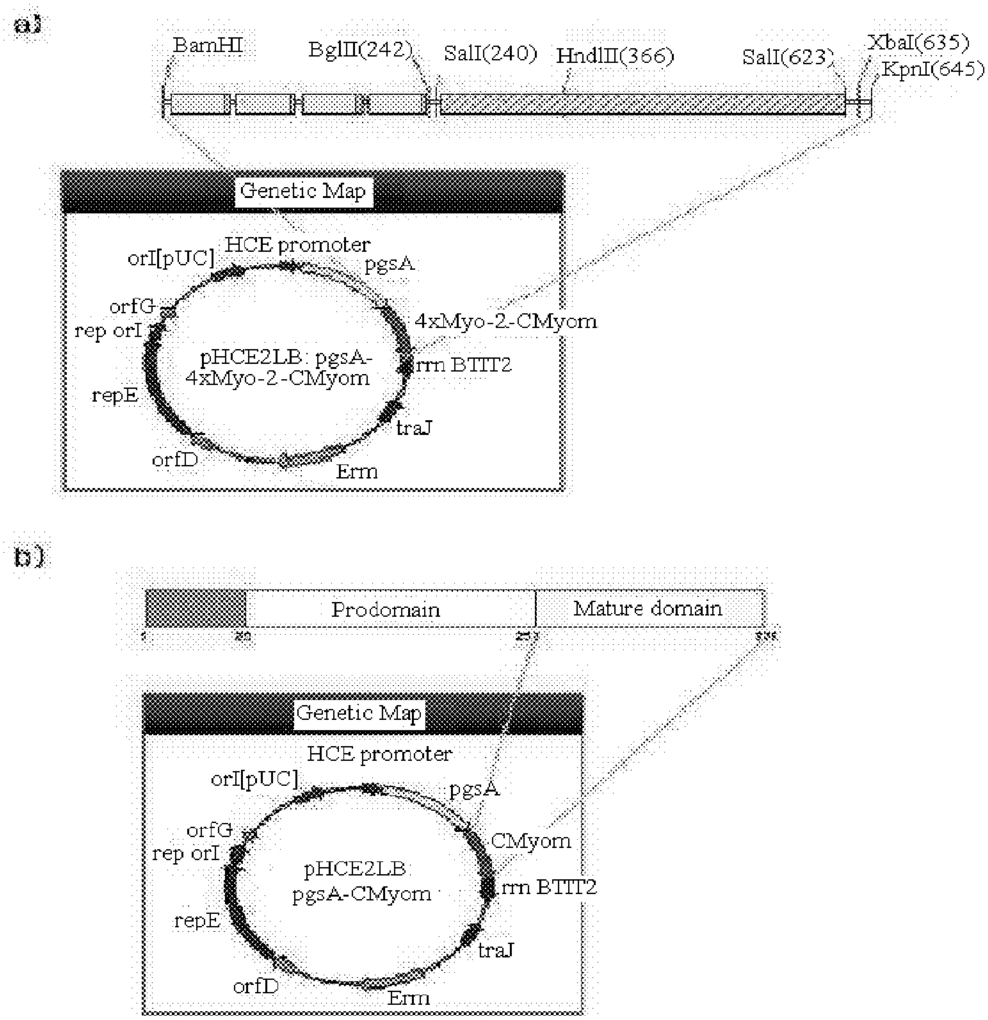
FIG. 4*a* shows a genetic map of the inventive surface expression vector pHCE2LB:pgsA-4-xMyo-2-CMyom expressing a fusion protein comprising a myostatin mature protein fused to a multimer of chicken myostatin-derived antigenic peptide (4xMyo-2)
FIG. 4*b* shows a genetic map of a surface expression vector pHCE2LB:pgsA-CMyom expressing a chicken myostatin mature protein.

Using a pgsA gene, among outer membrane protein genes pgsBCA involved in the synthesis of poly-gamma-glutamate derived from *Bacillus* sp. strains, pHCE2LB:pgsA-4xMyo-2-CMyom (FIG. 4*a*) and pHCE2LB:pgsA-CMyom (FIG. 4*b*) capable of expressing chicken myostatin mature protein and a gene encoding a target protein, in which a myostatin mature protein is fused to chicken myostatin 4xMyo-2, on the cell surface of gram-negative and gram-positive microorganisms as a host, were constructed.

4xMyo-2-CMyom obtained by digesting the constructed pRSET(A):4xMyo-2-CMyom with restriction enzymes BamHI and KpnI, and CMyom fragment obtained by PCR using a chicken myostatin gene cloned into pCR T7/NT-TOPO (Invitrogen, USA) were linked in accordance with decoding codon to the C-terminal end of the outer membrane protein gene pgsA involved in poly-gamma-glutamate synthesis of pHCE2LB:pgsA having the HPVL1 fragment of surface expression vector, pHCE2LB:pgsA-HPVL1 (KCTC 10349BP: *E. coli* transformed with pHCE2LB:pgsA-HPVL1) removed using BamHI and XbaI restriction sites, respectively.

Example 3

Cell Surface Expression of pgsA:4xMyo-2-CMyom and pgsA:CMyom

It was examined whether the fusion protein (pgsA:4xMyo-2-CMyom) in which a fusion protein, containing 4xMyo-2 peptide multimer fused to a mature protein, is fused to pgsA and the mature protein fused with pgsA (pgsA:CMyom) are expressed in *Lactobacillus* transformed with the surface expression vector pHCE2LB:pgsA-4xMyo-2-CMyom, comprising a gene encoding a myostatin fusion protein, and *Lactobacillus* transformed with the surface expression vector pHCE2LB:pgsA-4xMyo-2-CMyom, comprising a gene encoding a myostatin mature protein, which were constructed in Example 2.

For the expression of 4xMyo-2-CMyom protein and CMyom protein, respectively fused with the C-terminal end of the gene, pgsA involved in the synthesis of poly-gamma-glutamate, *Lactobacillus casei* strain transformed with pHCE2LB:pgsA-4xMyo-2-CMyom and *Lactobacillus casei* strain transformed with pHCE2LB:pgsA-CMyom were stationary-cultured in MRS medium (*Lactobacillus* MRS, Becton Dickinson and Company Sparks, USA) at 30° C., thus inducing the surface expression. The fusion protein expression was confirmed by SDS-polyacrylamide gel electrophoresis using the cultured cells and Western blotting using a pgsA-specific antibody.

In particular, the whole cell of the expression-induced *Lactobacillus casei* strain was denatured with protein obtained at the same cell concentration so as to prepare a sample. The sample was subjected to SDS-polyacrylamide gel electrophoresis, and transferred to PVDF (polyvinylidene-difluoride) membranes (Bio-Rad). The PVDF membranes to which the protein fractions have been transferred were blocked by shaking for 1 hour in a blocking buffer (50 mM Tris HCl, 5% skim milk, pH 8.0), and then, reacted for 1 hour with one thousand fold dilution of rabbit-derived polyclonal anti-pgsA primary antibodies in a blocking buffer. After completion of the reaction, the membranes were washed with buffer solutions and reacted for 1 hour with ten thousand fold dilution of HRP-conjugated anti-rabbit secondary antibodies in a blocking buffer. After completion of the reaction, the membranes were washed with buffer solution. The washed membranes were subjected to a color development process for 1 minute by the addition of a substrate (lumigen PS-3 acridan, $H_2O_2$), thus confirming the specific binding between the fusion proteins and pgsA-specific antibodies using CCD camera (FIG. 5).

Figure 5:
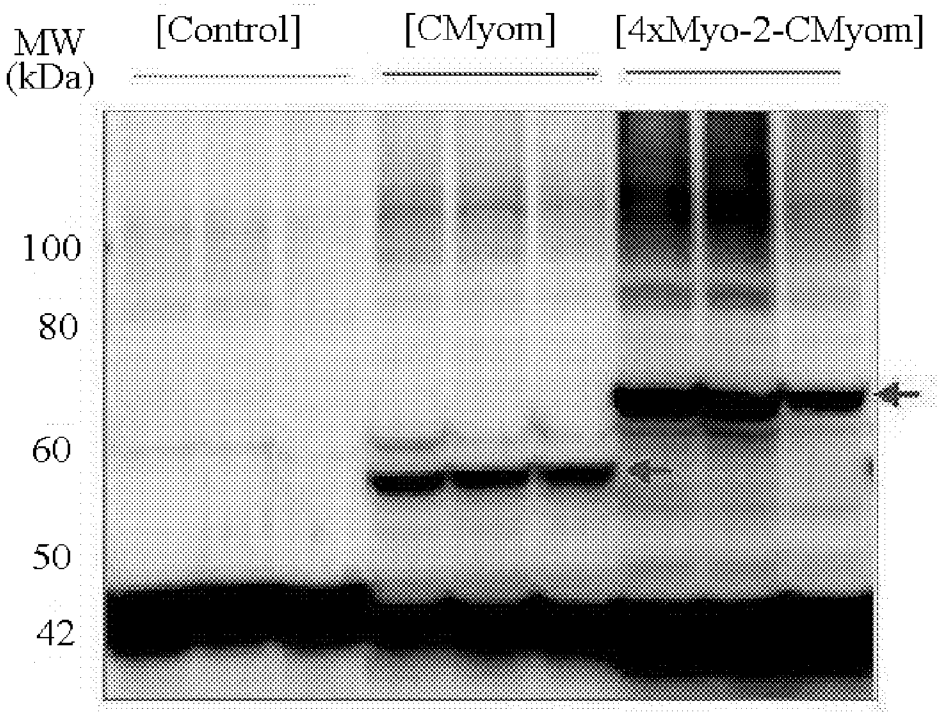
FIG. 5 shows the result of Western blot analysis using pgsA-specific antibodies on cells obtained by culturing lactic acid bacteria transformed with the inventive pHCE2LB:pgsA-4-xMyo-2-CMyom and pHCE2LB:pgsA-CMyom.

In FIG. 5, a control, CMyom and 4xMyo-2-CMyom represent *Lactobacillus casei* which was not transformed, *Lactobacillus casei*/pHCE2LB:pgsA-CMyom and *Lactobacillus casei*/pHCE2LB:pgsA-4xMyo-2-CMyom, respectively. As shown in FIG. 5, it was confirmed that the specific fusion protein pgsA-CMyom (about 55.5 kDa) and the specific fusion protein pgsA-4xMyo-2-CMyom (about 66.9 kDa) were present in the whole cells of each lactic acid bacteria. As a result, it was suggested that the bands of about 55.5 kDa and about 66.9 kDa are pgsA-CMyom fusion protein and pgsA-4xMyo-2-CMyom fusion protein, because pgsA has the size of about 42 kDa, CMyom protein has the size of about 13.5 kDa, and the 4xMyo-2-CMyom protein has the size of 24.9 kDa.

Example 4

Induction of Immune Response by *Lactobacillus* expressing 4xMyo-2-CMyom on the cell surface in mice and body weight change thereby

*Lactobacillus casei* having the fusion proteins expressed on their surface using the same method as described in Example 3 were orally administered to mice to examine immune response induction and body weight change induced by pgsA-4Myo-2-CMyom fusion protein and pgsA-CMyom fusion protein expressed on the surface of *Lactobacillus casei.*

Specifically, after *Lactobacillus casei*/pHCE2LB:pgsA-CMyom and *Lactobacillus casei*/pHCE2LB:pgsA-4xMyo-2-CMyom were cultured to collect cells, the collected cells were washed with PBS buffer (pH 7.4), and the *Lactobacillus* having the antigens expressed on the cell surface were orally administered to 6-week old C57BL/6 mice. At this time, two experimental groups (10 mice/group) were used in the experiment; group 1 treated with *Lactobacillus* expressing 4xMyo-2-CMyom fusion protein on their surface, and group 2 treated with *Lactobacillus* expressing CMyom protein on their surface. And they were orally administered to each group five times at an interval of one-day, and after one week, five times at an interval of one-day with a single dose of *Lactobacillus* ($5\times10^9$ cells) having the antigens expressed on their surface. And the broth, in which only the lactic acid bacteria were cultured, was administered to a control group, the C57BL/6 mice with the same schedule.

After 3 weeks of the initial oral administration, the mouse sera were collected and measured for IgG antibody titer against the 4xMyo-2-CMyom in serum by ELISA. FIG. **6*a*** shows the IgG antibody titer against the 4xMyo-2-CMyom in mouse serum, (A) is a group administered with the lactic acid bacteria expressing 4xMyo-2-CMyom on their surface, a test group (B) was administered with *Lactobacillus* expressing CMyom on their surface, and a control group (C) was administered with general *Lactobacillus casei.*

The purified 4xMyo-2-Myom fusion protein antigen was diluted to a concentration of 100 ng/100 μl with 0.1 M bicarbonate buffer ($NaHCO_3$, pH 9.6), added to an ELISA plate (100 μl/well) and reacted at 4° C. overnight. The plate was then washed three times with 300 μl/ml PBS-T (PBS+0.05% Tween 20), and 300/L of 5% skim milk was added to each well, then reacted for 3 hours at room temperature. After the plate was washed three times in the same manner as described above, Standard and $1^{st}$ antibody were diluted ranging from 1:10 to 1:6400 in 5% skim milk, and 100/L of diluent was added to each well, then reacted for 3 hours at room temperature. The wells were washed five times in the same manner as described above, and conjugate ($2^{nd}$ antibody) was diluted 1:5000 in 5% skim milk, then reacted for 1 hour at room temperature. Then, the wells were washed five times in the same manner as the above, and reacted with a color development reagent solution, TMB for 30 minutes to stop the color development with 50 μl of stop solution, then measured by an ELISA reader at 450 nm, thus examining antibody production against 4xMyo-2-CMyom fusion protein.

Figure 6:
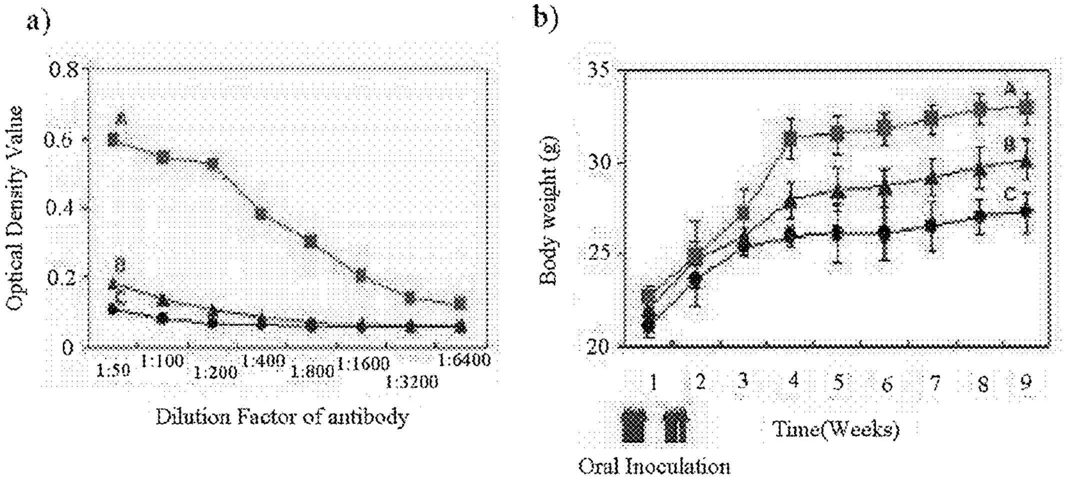
FIG. 6*a* shows antibody titers against 4xMyo-2-CMyom antigens in the sera of mice orally administered with *Lactobacillus casei* transformed with the inventive pHCE2LB:pgsA-4-xMyo-2-CMyom and pHCE2LB:pgsA-CMyom, which was measured by ELISA (Enzyme-linked immunosorbent assay)
FIG. 6*b* is the measurement results showing body weight changes in mice orally administered therewith (A: a group administrated with lactic acid bacteria transformed with pHCE2LB:pgsA-4-xMyo-2-CMyom; B: a group administrated with lactic acid bacteria transformed with pHCE2LB:pgsA-CMyom; C: a control group administered with general lactic acid bacteria).

As shown in FIG. 6*a*, it could be confirmed that, in the serum of C57BL/6 mice administered with *Lactobacillus casei* expressing 4xMyo-2-CMyom on the cell surface, the IgG antibody titers against 4xMyo-2-CMyom were significantly higher compared to the control group. Therefore, it was confirmed that microorganisms expressing the 4xMyo-2-CMyom fusion protein on the cell surface according to the present invention can effectively produce antibodies against the 4xMyo-2-CMyom fusion protein.

Additionally, after initial oral administration, weights of C57BL/6 mice were measured every week to compare and analyze the differences in their weights between the groups. As a result, as shown in FIG. 6*b*, from about 4 weeks after administration, the body weights of C57BL/6 mice in a group administrated with *Lactobacillus* expressing 4xMyo-2-CMyom on the cell surface were significantly higher than those of a group administered with *Lactobacillus casei* expressing CMyom and a control group, and significant differences in body weights, between the groups were observed with the passage of time. The phenomenon of enhanced weight gain was because antibodies against the inventive 4xMyo-2-CMyom fusion protein expressed on the surface of *Lactobacillus casei*, act to have the above effect.

Example 5

Inhibition Effect of Signaling in Mouse Muscle Cells by Antibodies, Induced by Lactic Acid Bacteria Expressing 4xMyo-2-CMyom Fusion Protein on their Surface After lactic acid bacteria expressing 4xMyo-2-CMyom fusion protein and lactic acid bacteria expressing CMyom protein on their surface were orally administered to mice using the same method as described in Example 4, in order to examine the inhibition effect of signaling in muscle cells, the ability of antibodies induced in the mice to neutralize myostatin in A-204 cells was measured at various concentrations.

Specifically, A-204 cell were dispensed into a 96-well plate at a density of $1\times10^5$ cells/well to culture for 24 hours in a $CO_2$ incubator, and 0.2 μg of pGL(CAGA)12 DNA and 0.5 μg of lipofectamine 2000 transfection reagent (lipofectamine 2000, Invitrogen, USA) were diluted in 50 μg of Opti-MEM, respectively, after 5 minutes, the media in two tubes were mixed and left to stand for 20 minutes. After that, 100 μl of the complex containing pGL(CAGA)12 DNA and lipofectamine 2000 was dispensed into each well of the 96-well plate containing A-204 cells, and 4~6 hours later, the culture medium of the 96-well plate was discarded and replaced with a fresh DMEM. After 24 hours, the cells were incubated in serum-free medium for 6 hours at 37° C. in a 5% $CO_2$ incubator. 10 ng/ml of myostatin (mGDF-8, R&D systems) diluted at various concentrations with mouse antibodies against myostatin protein was allowed to react on ice for 1 hour, and dispensed into each well of a 96-well plate to culture for 6 hours. The supernatant was assayed using luciferase assay system (Promega, USA) to measure luciferase activity in A-204 cells induced by signaling of unreacted myostatin protein remained after reaction with the antibodies, thus measuring the ability of antibodies to neutralize myostatin in A-204 cells.

Figure 7:
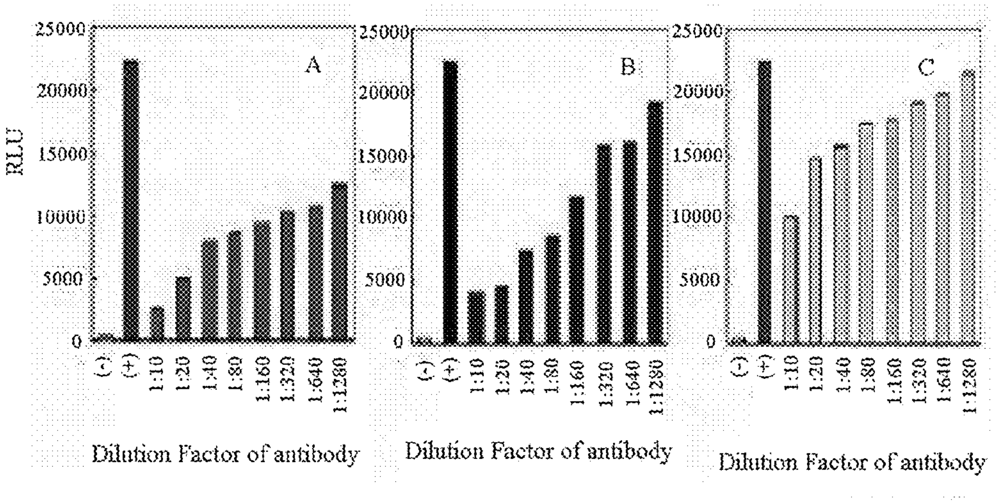
FIG. 7 shows the inhibition effect of signaling in muscle cells by antibodies present in the sera of mice which were orally administered with *Lactobacillus casei* transformed with the inventive pHCE2LB:pgsA-4-xMyo-2-CMyom and pHCE2LB:pgsA-CMyom (A: a group administrated with lactic acid bacteria expressing a fusion protein, 4xMyo-2-CMyom on the cell surface; B: a group administrated with lactic acid bacteria expressing CMyom on the cell surface; C: a control group administered with general lactic acid bacteria).

FIG. 7 shows inhibition effect of mouse serum myostatin signaling in muscle cells, examined by measuring luciferase activity. A is a group administered with lactic acid bacteria expressing 4xMyo-2-CMyom fusion protein on the cell surface, B is a group administered with lactic acid bacteria expressing CMyom protein on the cell surface, and C is a control group administered with general lactic acid bacteria. As a result, the group administered with 4xMyo-2-CMyom fusion protein induced the highest level of antibody, suggesting that the 4xMyo-2-CMyom-administered group has remarkably significant effect on the inhibition of myostatin signaling in muscle cells.

Example 6

Induction of Immune Response by *Lactobacillus* Expressing the Fusion Protein of 4xMyo-2-CMyom on the Cell Surface in Broilers and Body Weight Change Thereby Using *Lactobacillus casei*/pHCE2LB:pgsA-4xMyo-2-CMyom, the induction of immune response against 4xMyo-2-CMyom fusion protein and body weight change in broiler chickens, were examined.

The experiment was carried out using assorted feed for Cobb broiler chickens, which is mixed with *Lactobacillus casei*/pHCE2LB:pgsA-4xMyo-2-CMyom. Specifically the transformed lactic acid bacteria were cultured, and harvested, then washed with a buffer solution (PBS, pH 7.4) to lyophilize, thus mixing with the assorted feed to use for the experiment.

An experimental group consisting of 72 Cobb female broiler chickens and a control group consisting of 72 Cobb female broiler chickens were used for the experiment and they were reared for 6 weeks. The experimental group was fed with the assorted feed mixed with 0.2% lyophilized powder ($8.1\times10^5$ cells/g) of lactic acid bacteria expressing 4xMyo-2-CMyom on the cell surface at 1, 2 and 3 weeks, and fed with the assorted feed alone at 4, 5, and 6 weeks. The control group was fed with only assorted feed from week 1 to week 6.

6 weeks after the start of the experiment, chicken sera of the experimental and the control groups were taken, and IgG antibody titer against chicken myostatin mature protein in the chicken sera was measured by ELISA.

Figure 8:
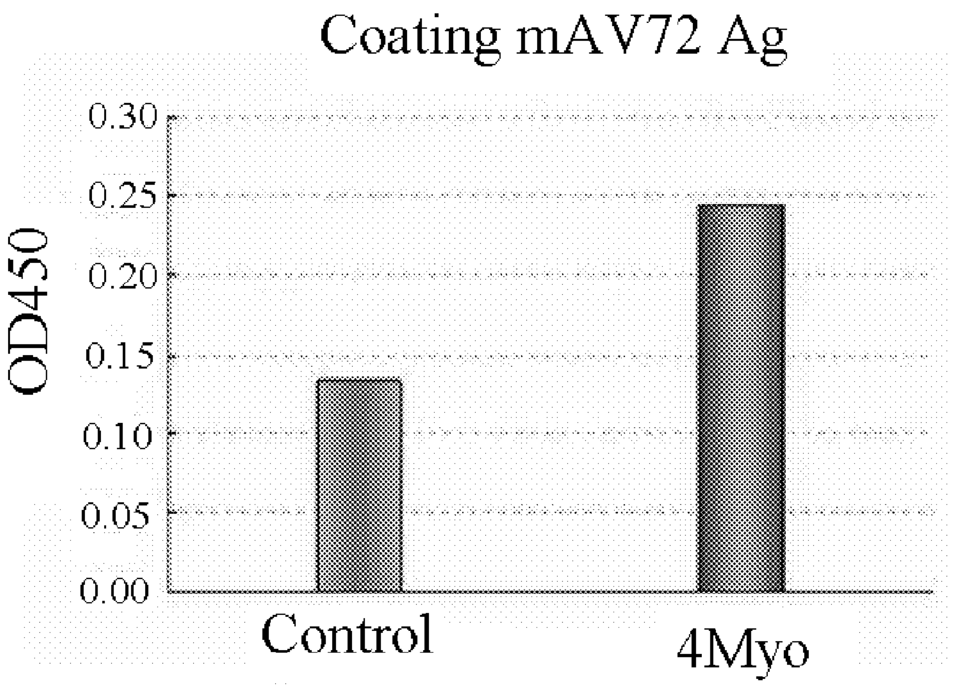
FIG. 8 shows IgG antibody titers against chicken myostatin mature antigens in the sera of chicks orally administered with *Lactobacillus casei* through feed, which has been transformed with the inventive pHCE2LB:pgsA-4-xMyo-2-CMyom to have 4xMyo-2-CMyom expressed on the surface thereof, measured by ELISA.

As a result, as shown in FIG. 8, it could be confirmed that the antibody titer of the experimental group, fed with the assorted feed mixed with lyophilized powder of lactic acid bacteria having 4xMyo-2-CMyom fusion protein expressed on the surface thereof, was higher than that of the control group fed with only the assorted feed. Thus, it could be seen that the antibodies against the myostatin mature protein were effectively produced in chicks by the lactic acid bacteria having 4xMyo-2-CMyom fusion protein expressed on the surface thereof.

In addition, body weights of chicks in the experimental group fed with lactic acid bacteria expressing 4xMyo-2-CMyom fusion protein on their surface and chicks in the control group fed with general lactic acid bacteria were measured every week to analyze the difference in body weights of chicks between groups.

Figure 9:
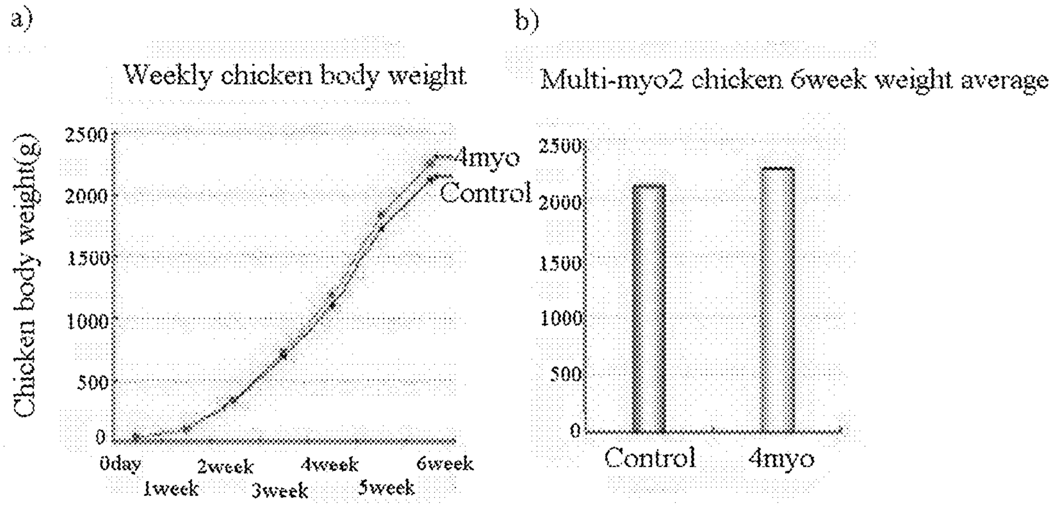
FIG. 9*a* is the measurement results showing body weight changes in chicks orally administered with *Lactobacillus casei* through feed, which has been transformed with the inventive pHCE2LB:pgsA-4-xMyo-2-CMyom to have 4xMyo-2-CMyom expressed on the surface thereof.
FIG. 9*b* shows average body weights of chicks at the completion of the experiment (6 weeks).

As a result, as shown in FIG. 9*a*, in the graph showing weight differences between the control group and the experimental group, it was observed that weight difference between two groups increased every week. Additionally, as a result of comparing and analyzing average body weights of mice in the experimental group and the control group after 6 weeks, as shown in FIG. 9*b*, in the experimental group, the average body weight was increased by 6.6% compared to the control group. The phenomenon of enhanced weight gain was because antibodies against the inventive 4xMyo-2-CMyom fusion protein expressed on the surface of *Lactobacillus casei*, act to have the above effect.

Figure 10:
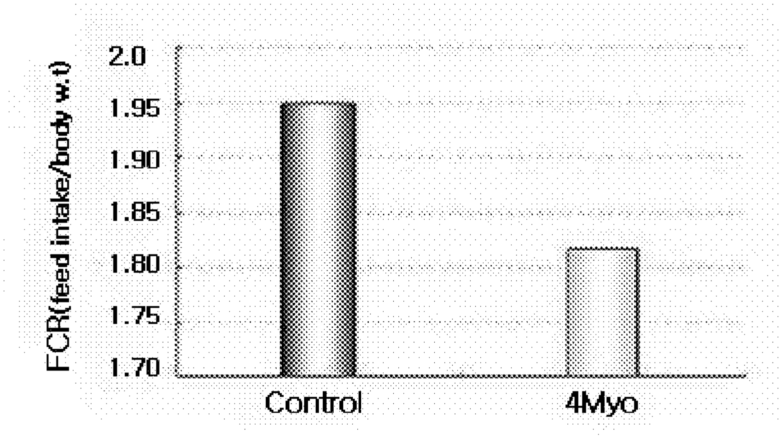
FIG. 10 shows feed efficiency in chicks orally administered with *Lactobacillus casei* through feed, which has been transformed with the inventive pHCE2LB:pgsA-4-xMyo-2-CMyom to have 4xMyo-2-CMyom expressed on the surface thereof.

In addition, the feedstuff efficiency of the experimental group and the control group was measured and expressed as a graph showing feed intake/body weight. As a result, as shown in FIG. 10, in the experimental group, the feedstuff efficiency increased by 7.4% compared to the control group.

INDUSTRIAL APPLICABILITY

As described above in detail, the feedstuff additive or pharmaceutical composition according to the present invention can be used for muscle development and regulation of muscle growth in livestock and poultry, as well as for preventing and treating muscle-wasting diseases and degenerative diseases such as muscular dystrophy, muscular atrophy and the like. In addition, the transformed strain shows the same effect even if the strain itself after culture thereof is directly used, and thus it is very economical.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A nucleic acid surface expression vector for expression of a myostatin fusion protein in a cell, comprising:

one or more than two genes encoding a poly-gamma-glutamate synthetase complex selected from the group consisting of pgsB, pgsC and pgsA, operatively linked to a gene encoding a fusion protein comprising a myostatin mature protein fused with a Myo-2 peptide multimer consisting of 2 to 8 of an isolated Myo-2 peptide, wherein each Myo-2 peptide consist of the amino acid sequence of SEQ ID NO: 1.

2. The expression vector according to claim 1, wherein said Myo-2 peptide is isolated from mammals or birds.

3. A recombinant bacterium which is obtained by transforming a bacterium selected from the group consisting of Gram-negative bacteria and Gram-positive bacteria with the expression vector according to claim 1, wherein upon expression, the fusion protein is expressed on the cell surface.

4. The bacterium according to claim 3, wherein the bacterium is selected from the group consisting of *E. coli, Salmonella typhi, Salmonella typhimurium, Vibrio cholerae, Mycobacterium bovis, Shigella, Bacillus*, lactic acid bacteria, *Staphylococcus, Corynebacteria, Listeria monocytogenes* and *Streptococcus*.

5. The bacterium according to claim 4, wherein the bacterium is lactic acid bacteria.

6. An isolated Myo-2 peptide from myostatin consisting of the amino acid of sequence of SEQ ID NO: 1.

7. A Myo-2 peptide multimer consisting of 2 to 8 of the Myo-2 peptide of claim 6.

8. A fusion protein comprising a myostatin mature protein fused with a Myo-2 peptide multimer consisting of 2 to 8 of an isolated Myo-2 peptide, wherein each Myo-2 peptide consist of the amino acid sequence of SEQ ID NO: 1.

9. A feedstuff additive for promoting muscle growth or improving body weight gain in animals, which comprises the fusion protein of claim 8 as an effective ingredient.

10. A composition for promoting muscle growth or improving body weight gain in animals, which comprises the fusion protein of claim 8 as an effective ingredient.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: Myo-2 peptide

<400> SEQUENCE: 1

Val Phe Leu Gln Lys Tyr Pro His Thr His Leu Val His Gln Ala
1               5                   10                  15


<210> SEQ ID NO 2
<211> LENGTH: 24
<212> TYPE: PRT
<213> ORGANISM: Artificial Sequence
<220> FEATURE:
<223> OTHER INFORMATION: Myo-1 peptide

<400> SEQUENCE: 2

Met Ser Pro Ile Asn Met Leu Tyr Phe Asn Gly Lys Glu Gln Ile Ile
1               5                   10                  15

Tyr Gly Lys Ile Pro Ala Met Val
            20


<210> SEQ ID NO 3
<211> LENGTH: 122
<212> TYPE: PRT
<213> ORGANISM: Gallus sp.

<400> SEQUENCE: 3

Glu Val Arg Val Thr Asp Thr Pro Lys Arg Ser Arg Arg Asp Phe Gly
1               5                   10                  15

Leu Asp Cys Asp Glu His Ser Thr Glu Ser Arg Cys Cys Arg Tyr Pro
            20                  25                  30

Leu Thr Val Asp Phe Glu Ala Phe Gly Trp Asp Trp Ile Ile Ala Pro
        35                  40                  45

Lys Arg Tyr Lys Ala Asn Tyr Cys Ser Gly Glu Cys Glu Phe Val Phe
    50                  55                  60

Leu Gln Lys Tyr Pro His Thr His Leu Val His Gln Ala Asn Pro Arg
65                  70                  75                  80

Gly Ser Ala Gly Pro Cys Cys Thr Pro Thr Lys Met Ser Pro Ile Asn
                85                  90                  95

Met Leu Tyr Phe Asn Gly Lys Glu Gln Ile Ile Tyr Gly Lys Ile Pro
            100                 105                 110

Ala Met Val Val Asp Arg Cys Gly Cys Ser
```

-continued 115 120

<210> SEQ ID NO 4
<211> LENGTH: 1128
<212> TYPE: DNA
<213> ORGANISM: Gallus sp.

<400> SEQUENCE: 4
atgcaaaagc tagcagtcta tgtttatatt tacctgttca tgcagatcgc ggttgatccg 60
gtggctctgg atggcagtag tcagcccaca gagaacgctg aaaaagacgg actgtgcaat 120
gcttgtacgt ggagacagaa tacaaaatcc tccagaatag aagccataaa aattcaaatc 180
ctcagcaaac tgcgcctgga acaagcacct aacattagca gggacgttat taagcagctt 240
ttacccaaag ctcctccact gcaggaactg attgatcagt atgatgtcca gagggacgac 300
agtagcgatg gctctttgga agacgatgac tatcatgcca caaccgagac gattatcaca 360
atgcctacgg agtctgattt tcttgtacaa atggagggaa aaccaaaatg ttgcttcttt 420
aagtttagct ctaaaataca atataacaaa gtagtaaagg cacaattatg gatatacttg 480
aggcaagtcc aaaaacctac aacggtgttt gtgcagatcc tgagactcat taagcccatg 540
aaagacggta caagatatac tggaattcga tctttgaaac ttgacatgaa cccaggcact 600
ggtatctggc agagtattga tgtgaagaca gtgctgcaaa attggctcaa acagcctgaa 660
tccaatttag gcatcgaaat aaaagctttt gatgagactg gacgagatct tgctgtcaca 720
ttcccaggac cgggtgaaga tggattgaac ccatttttag aggtcagagt tacagacaca 780
ccgaaacggt cccgcagaga ttttggcctt gactgtgatg agcactcaac ggaatcccga 840
tgttgtcgct acccgctgac agtggatttc gaagcttttg gatgggactg gattatagca 900
cctaaaagat acaaagccaa ttactgctcc ggagaatgcg aatttgtgtt tctacagaaa 960
tacccgcaca ctcacctggt acaccaagca aatcccagag gctcagcagg cccttgctgc 1020
acacccacca agatgtcccc tataaacatg ctgtatttca atggaaaaga acaaataata 1080
tatggaaaga taccagccat ggttgtagat cgttgcgggt gctcatga 1128

<210> SEQ ID NO 5
<211> LENGTH: 70
<212> TYPE: DNA
<213> ORGANISM: Artificial Sequence
<220> FEATURE:
<223> OTHER INFORMATION: Synthetic Construct

<400> SEQUENCE: 5
gatccgtttt tcttcaaaag tatccacata cacatcttgt tcatcaagct ggtggttcaa 60
gatctggtac 70

<210> SEQ ID NO 6
<211> LENGTH: 62
<212> TYPE: DNA
<213> ORGANISM: Artificial Sequence
<220> FEATURE:
<223> OTHER INFORMATION: Synthetic Construct

<400> SEQUENCE: 6
cagatcttga accaccagct tgatgaacaa gatgtgtatg tggatacttt tgaagaaaaa 60
cg 62

<210> SEQ ID NO 7
<211> LENGTH: 30
<212> TYPE: DNA

-continued

```
<213> ORGANISM: Artificial Sequence
<220> FEATURE:
<223> OTHER INFORMATION: Synthetic Construct

<400> SEQUENCE: 7

agatctgtcg acgaggtcag agttacagac                                  30


<210> SEQ ID NO 8
<211> LENGTH: 42
<212> TYPE: DNA
<213> ORGANISM: Artificial Sequence
<220> FEATURE:
<223> OTHER INFORMATION: Synthetic Construct

<400> SEQUENCE: 8

ggtacctcta gattattagt cgactcatga gcacccgcaa cg                    42
```